US012629383B2

(12) United States Patent
Pisak

(10) Patent No.: US 12,629,383 B2
(45) Date of Patent: May 19, 2026

(54) CANNABINOID COMPOSITIONS WITH HIGH SOLUBILITY AND BIOAVAILABILITY

(71) Applicant: Mehmet Nevzat Pisak, Istanbul (TR)

(72) Inventor: Mehmet Nevzat Pisak, Istanbul (TR)

( * ) Notice: Subject to any disclaimer, the term of this patent is extended or adjusted under 35 U.S.C. 154(b) by 276 days.

(21) Appl. No.: 17/309,559

(22) PCT Filed: Nov. 19, 2020

(86) PCT No.: PCT/IB2020/060914
§ 371 (c)(1),
(2) Date: Jun. 4, 2021

(87) PCT Pub. No.: WO2021/123960
PCT Pub. Date: Jun. 24, 2021

(65) Prior Publication Data
US 2022/0362207 A1    Nov. 17, 2022

(51) Int. Cl.
| | |
|---|---|
| *A61K 31/00* | (2006.01) |
| *A61K 9/00* | (2006.01) |
| *A61K 9/107* | (2006.01) |
| *A61K 9/20* | (2006.01) |
| *A61K 47/02* | (2006.01) |
| *A61K 47/12* | (2006.01) |
| *A61K 47/40* | (2006.01) |

(52) U.S. Cl.
CPC .......... *A61K 31/658* (2023.05); *A61K 9/0053* (2013.01); *A61K 9/107* (2013.01); *A61K 9/2009* (2013.01); *A61K 9/2018* (2013.01); *A61K 9/205* (2013.01); *A61K 47/02* (2013.01); *A61K 47/12* (2013.01); *A61K 47/40* (2013.01)

(58) Field of Classification Search
CPC .... A61K 31/352; A61K 9/0053; A61K 9/107; A61K 9/2009; A61K 9/2018; A61K 9/205; A61K 31/05; A61K 47/02; A61K 47/12; A61K 47/40; A61K 9/0056; A61K 9/006; A61K 9/2095; A61K 31/192; A61K 9/143
See application file for complete search history.

(56) References Cited

U.S. PATENT DOCUMENTS

| | | | | |
|---|---|---|---|---|
| 2011/0028431 A1* | 2/2011 | Zerbe | ...................... | A61P 25/06 |
| | | | | 514/58 |
| 2012/0231083 A1* | 9/2012 | Carley | ................... | A61K 9/146 |
| | | | | 424/490 |
| 2012/0263785 A1* | 10/2012 | Rossi | ..................... | A61K 31/05 |
| | | | | 53/403 |
| 2014/0357708 A1* | 12/2014 | Murty | ................... | A61K 47/10 |
| | | | | 514/454 |
| 2016/0184258 A1* | 6/2016 | Murty | ................. | A61K 31/655 |
| | | | | 514/454 |
| 2018/0263913 A1* | 9/2018 | Lefler | ................. | A61K 31/352 |
| 2018/0263953 A1* | 9/2018 | Renwick | ............. | A61K 36/185 |

FOREIGN PATENT DOCUMENTS

| | | | | |
|---|---|---|---|---|
| WO | WO-2016022936 A1 * | 2/2016 | ........... | A61K 31/352 |

* cited by examiner

*Primary Examiner* — Deborah D Carr
(74) *Attorney, Agent, or Firm* — Lisa Mueller; Casimir Jones SC

(57) ABSTRACT

The present invention is based on the highly soluble and bioavailable cannabinoid compositions which can be made at a commercial scale with a simple manufacturing process. Thus, the present invention relates to oral compositions comprising a cannabinoid compound, for use in the nutraceutical, pharmaceutical, food or beverage industries and its production methods.

22 Claims, No Drawings

CANNABINOID COMPOSITIONS WITH HIGH SOLUBILITY AND BIOAVAILABILITY

TECHNICAL FIELD

The present invention relates to a composition comprising a cannabinoid compound, at least one emulsifier, at least one acid component and optionally comprising a dextrin compound and at least one silica derivative to be used in oral formulations.

BACKGROUND ART

Plants within the genus Cannabis, have been cultivated for thousands of years in many parts of the world and has three main subspecies: Indica, sativa, and ruderalis. Medical preparations of the cannabis plant have been observed to produce analgesic, anti-anxiety, anti-spasmodic, muscle relaxant, anti-inflammatory and anticonvulsant effects among many others. It is also of note that cannabinoids are being used for the treatment of cancer, and cancer related applications such as chemotherapy induced nausea and several different neurological disorders including Parkinson's and epilepsy. The cannabinoids within the cannabis plant can also be further isolated to increase the amount of a particular cannabinoid within a composition.

Cannabis as a plant contains many different cannabinoids: Cannabidiol (CBD) and Δ9-tetrahydrocannabinol (THC) are the most studied ones. They both act through cannabinoid receptors and have therapeutic effects, but THC has psycho-active properties whereas CBD is not intoxicating under normal circumstances. Although THC and CBD have been the most studied cannabinoids, there are many others identified to date including but not limited to; cannabinol (CBN), cannabigerol (CBG), Cannabidivarin (CBDV), and Tetrahydrocannabivarin (THCV). There are also synthetic cannabinoids such as dronabinol and nabilone and other synthetic analogues being developed for a variety of indications.

Cannabinoids are usually inhaled or taken orally; the rectal route, sublingual administration, transdermal delivery, eye drops, and aerosols have been used in only a few studies and are of little relevance in practice today. The pharmacokinetics of THC or CBD vary as a function of its route of administration. Oral bioavailability of cannabinoids is significantly low compared to inhalation and this poses a health issue wherein most of the patients are inevitably guided towards smoking compounds with cannabinoid content in order to get their full benefit.

All known cannabinoids, especially CBD and THC are known to be highly lipophilic and thus have very low water solubility. They also have very low bioavailability which limits the form and mode of administration. Cannabinoids, especially CBD has also found wide use as a supplement and functional food. It is also being used in beverages and food products for general well-being purposes encompassing anxiety, sleeplessness (insomnia), pain and inflammatory diseases. However, the effectiveness of cannabinoids as a medicinal product, supplement or functional food/beverage is all limited due to its low bioavailability (BA) caused by the poor absorption of cannabinoids due to low solubility and low permeability. Thus, it is difficult to obtain effective blood concentrations.

In the state of the art, there have been multiple studies to overcome the issue of cannabinoid solubility and bioavailability some of which include includes co-solvency, micellization, (nano)-(micro)-emulsification, inclusion complexes, encapsulation in lipid-based formulations and nanoparticle delivery strategies. U.S. Pat. No. 7,423,026B2 discloses complexes of methylated cyclodextrin with cannabinoids. Similarly, US20050153931A1 discloses a cannabinoid/cyclodextrin infusion complex in order to solve the dissolution problem of cannabinoids.

U.S. Pat. No. 9,265,724B2 discloses self-emulsifying drug delivery systems wherein the cannabinoids are dissolved in an oily medium together with at least one surfactant to increase the solubility and bioavailability of the active compounds.

U.S. Pat. No. 8,222,292B2 discloses a solvent, co solvent formulation of dronabiol that increase the in-vivo absorption of the cannabinoid (dronabiol) which also includes the emulsifier polyethylene glycol. Yet this composition has alcoholic content as an undesirable aspect of the invention. And the preferred embodiment of the present invention has no alcohol content or similar organic solvent.

US20120295968A1 discloses oral formulation containing CBD (cannabinoid) and THC (tetrahydrocannabinol) with a small molecule selected from citric acid, ascorbic acid, citrus essential oil(s), lecithin, one or more sugar(s), resvertrol and their combination. The main purpose of the invention is about enhancing the psychoactivity of THC. Furthermore the patent discloses that the composition of THC, CBD, and one or more small molecules, as described herein, promotes and maintains a more balanced metabolism at the intracellular-level by positively modulating the Citric Acid Cycle but does not refer nor present any data referring to an increase in the solubility nor bioavailability of cannabinoids, moreover it does not explain the effects of the composition on the degradation of the cannabinoid(s) probably due to the low cannabinoid to acid component ratios.

U.S. Pat. No. 8,980,940B2 discloses that citric acid, alternatively, a mineral acid may be used, and may be chosen from phosphoric acid, hydrochloric acid, nitric acid and sulphuric acid. In one embodiment the composition comprises a combination of different acids, optionally a combination of at least one organic acid with at least one mineral acid. It is disclosed that weak acids have an especially positive stabilizing effect on (−)-Δ9-trans-THC and its derivatives, forming a stabilized composition. But, the invention does not aim to increase the solubility and bioavailability of the cannabinoids. The extremely low ratios of the acid component used in the formulation also shows that the acids are only used for stabilization.

Moreover, both US20120295968A1 and U.S. Pat. No. 8,980,940B2 do not disclose the use of emulsifiers with pH decreasing agents. And the effect it would have on the solubility or bioavailability of cannabinoids.

In addition, it has been also shown in the prior art that an acidic environment degrades cannabinoids, creates impurities and even transforms some of them into other cannabinoids as demonstrated by Watanabe et al. ((June 2007) Forensic Toxicology 25(1):16-21).

Thus, there is still a need in the art for compositions enhancing the solubility and the bioavailability of cannabinoids by using a safe formulation which is also stable, easy to manufacture and not expensive. However, there is still a need in the art for an oral composition enhancing the solubility and the bioavailability of cannabinoid compounds, which is also stable, easy to manufacture and not expensive.

SUMMARY OF THE INVENTION

The present invention provides an oral composition comprising a cannabinoid compound solving the solubility and bioavailability problems in the prior art.

In one aspect, the present invention relates to an oral composition comprising at least one cannabinoid compound, at least one emulsifier and at least one acid component.

In another aspect, the composition of the present invention preferably contains an organic acid as acid component or more preferably an acid component which is selected from the group consisting of stearic acid, citric acid, gluconic acid (E 574), inosinic acid (E 630), glutamic acid (E620), guanilic acid (E 626), sodium caprate (decanoic acid), dichroic acid (E330), malic acid (E296), acetic acid (E260), tartaric acid (E334), lactic acid (E270), alginic acid (E400), or a mixture thereof and most preferably stearic acid, citric acid or decanoic acid (sodium caprate).

In another aspect, the present invention provides a composition comprising a cannabinoid, at least one organic acid with at least one emulsifier having a HLB value between 10 and 25.

In another aspect, the emulsifier is preferably selected from the group consisting of polyoxethylene derivatives, sorbitan esters, polyethylene glycol derivatives and a combination thereof. Polyoxethylene can be polyoxyglycerides such as stearoyl polyoxyl-32 glycerides, lauroyl polyoxyl-32 glycerides or polyoxy-ethylene sucrose diester dimyristate, Polyoxy-ethylene sucrose diester dinnyristate, polyoxy-ethylene sucrose diester dipalmitate, polyoxy-ethylene sucrose diester dioleate; sorbitan esters can be polysorbate 80, polysorbate 60, polysorbate 20; polyethylene glycol derivatives can be PEG-8 laurate, PEG 400 monoluarate, PEG 10 isooctylphenyl ether, PEG 40 stearate, PEG 50 stearate, PEG 40 isooctylphenyl ether, and others selected from sodium stearoyl-2-lactylate, sodium stearoyl lactylate.

In another aspect, the ratio of the emulsifier to the acid component is between 40:1 to 20:1. and preferably 30:1 to 20:1 and most preferably 30:1 to 15:1.

In another aspect, the composition of the present invention comprises at least one dextrin compound and optionally at least one silica derivative.

DETAILED DESCRIPTION OF THE INVENTION

The present invention relates to an oral composition comprising at least one cannabinoid compound, at least one emulsifier and at least one acid component.

Acid component(s) or pH decreasing agent(s) are another integral part of the composition along with the emulsifier(s). The composition of the present invention preferably contains an organic acid as acid component or more preferably an acid component which is selected from the group consisting of stearic acid, citric acid, gluconic acid (E 574), inosinic acid (E 630), glutamic acid (E620), guanilic acid (E 626), sodium caprate (decanoic acid), dichroic acid (E330), malic acid (E296), acetic acid (E260), tartaric acid (E334), lactic acid (E270), alginic acid (E400), or a mixture thereof.

According to the present invention, the composition comprises at least one acid component in an amount from 1 to 100 mg, preferably 5 to 100 mg and more preferably 10 to 100 mg, most preferably 10 to 75 mg per oral unit dose.

As demonstrated by the formulation examples of the present invention, the inventor has found that the addition of an acid component significantly ameliorates the bioavailability and dissolution profile of the cannabinoid. In addition, it has been also found that the combination of the acid component with at least one emulsifier preferably in specific ratios, a synergistic effect in the dissolution profile of cannabinoid is shown. It is seen that the use of acid component with an emulsifier causes a micelle formulation which enhances the dissolution of cannabinoid.

The composition of the present invention comprises most preferably stearic acid, citric acid or decanoic acid (sodium caprate). They surprisingly provide a better dissolution profile compared with other acid components.

As used herein, the term "cannabinoid compound" means that substances obtained from the cannabis plant, which includes Cannabis sativa, Cannabis indica, Cannabis Ruderalis and variants thereof, cannabis chemovars which contain differing amounts of individual cannabinoids, which are extracted with the use of a solvent and/or through $CO_2$ extraction. The term "cannabinoid compound" also means highly purified compounds with very high levels of cannabinoid content, which are obtained through synthesis or using fermentation.

Thus, cannabinoid compounds may be extract of cannabis plants, synthetic cannabinoids or fermented cannabinoids. In addition, they can be a combination of such cannabinoid compounds from different sources which are all void of good aqueous solubility.

The cannabinoid compound is selected from the group consisting of;

Cannabichromenes: Cannabichromene (CBC), Cannabichromenic acid (CBCA), Cannabichromevarin (CBCV), Cannabichromevarinic acid (CBCVA)

Cannabicyclols: Cannabicyclol (CBL), Cannabicyclolic acid (CBLA), Cannabicyclovarin (CBLV)

Cannabidiols: Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA)

Cannabielsoins: Cannabielsoic acid B (CBEA-B), Cannabielsoin (CBE), Cannabielsoin acid A (CBEA-A)

Cannabigerols: Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA)

Cannabinols: Cannabinodiol (CBND), Cannabinodivarin (CBVD), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV)

Cannabitriols: 10-Ethoxy-9-hydroxy-delta-6a-tetrahydrocannabinol, 8,9-Dihydroxy-delta-6a-tetrahydrocannabinol, Cannabitriol (CBT), Cannabitriolvarin (CBTV)

Delta-8-tetrahydrocannabinols: Delta-8-tetrahydrocannabinol (Δ8-THC), Delta-8-tetrahydrocannabinolic acid (Δ8-THCA)

Delta-9-tetrahydrocannabinols: Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA)

Other cannabinoids: 10-Oxo-delta-6a-tetrahydrocannabinol (OTHC), Cannabichromanon (CBCF), Cannabifuran (CBF), Cannabiglendol, Cannabiripsol (CBR), Cannbicitran (CBT), Dehydrocannabifuran (DCBF), Delta-9-cis-tetrahydrocannabinol (cis-THC), Tryhydroxy-delta-9-tetrahydrocannabinol (triOH-THC), 3,4, 5,6-Tetrahydro-7-hydroxy-alpha-alpha-2-trimethyl-9-n-propyl-2,6-methano-2H-1-benzoxocin-5-methanol, (OH-iso-HHCV)

The cannabinoid compound is preferably selected from the group consisting of Δ9-tetrahydrocannabinol (THC), Δ8-tetrahydrocannabinol, Δ9-tetrahydrocannabinol propyl analogue (THCV), cannabidiol (CBD), cannabidiol propyl analogue (CBDV), cannabinol (CBN), cannabichromene, cannabichromene propyl analogue and cannabigerol or any combination thereof.

The cannabinoid compound is more preferably selected from the group consisting of Cannabidiols (CBD), Delta-9-tetrahydrocannabinols (THC), Cannabigerols and Cannabitriols or derivatives thereof.

Cannabinoid compounds can be solid, semi-solid or liquid such as powder form, paste, oil or solution.

According to the present invention, the composition can comprise a cannabinoid compound in an amount of from 1 to 300 mg, preferably 1 to 200 mg more preferably 1 to 100 mg, and most preferably 1 to 60 mg per oral unit dose. Amounts are based on the pure amount of cannabinoid, e.g.: if a 100 mg of distillate or isolate powder has 2% of pure CBD, THC, THCV or CBG content, the amount of cannabinoid would be equal to 2 mg.

The emulsifier of the present invention has an HLB value between 10 and 25, preferably between 10 and 21.

As used herein, HLB means hydrophilic-lipophilic balance (HLB), i.e. the balance of the size and strength of the hydrophilic (water-loving or polar) and the lipophilic (oil-loving or non-polar) groups of the emulsifier. In the HLB system, each emulsifier is assigned a numerical value which is called its HLB. The HLB of emulsifiers is shown in all current ICI emulsifier literature, and similar values may be calculated or estimated by various means for any emulsifier. All emulsifiers consist of a molecule that combines both hydrophilic and lipophilic groups. An emulsifier that is lipophilic in character is assigned a low HLB number (below 9.0), and one that is hydrophilic is assigned a high HLB number (above 10.0). Those in the range of 9-11 are intermediate.

According to the present invention, the emulsifier is selected from, but not limited to the group consisting of PEG-7 Glyceryl Cocoate, PEG-20 Almond Glycerides, PEG 40 Sorbitane Hexaoleate, PEG 40 Sorbitane Perisosteareate, PEG 10 Olive Glycerides, PEG-8 caprylic/capric glycerides (Labrafac CM 10-Gattefosse), Polyoxyethylene oleyl ether (EMULGEN 408-EMULGEN 430) respectively HLB=10-16.2, PEG Sorbilate Hexa oleate, Polysorbate 65 PE(20) sorbitan tristearate, Polyoxyethylene lauryl ether (G-3705), Polyoxyethylene lauryl ether (EMULGEN 106-EMULGEN 108-EMULGEN 109P-EMULGEN 120-EMULGEN 123P-EMULGEN 147-EMULGEN 150, PEG 25 Hydrogenated Castor Oil, Polyoxyethylene monostearate (Myrj 45), PEG 7 Glyceryl Cocoate (Sympatens-GMC/070), Glyceryl Stearate (and) PEG-100 Stearate Polysorbate 85, PEG-7 Olivate, PEG-20 sorbitan trioleate (Tween-85 Atlas/ICI), PEG-20 sorbitan tristearate (Tween 65 Atlas/ICI), PEG-25 hydrogenated castor oil (Simulsol 1292 Seppic), PEG-25 hydrogenated castor oil (Cerex ELS 250 Auschem SpA), PEG-25 trioleate (Tagat TO Goldschmidt), Polysorbate 85, PEG 8 Stearate, PEG 400 Monoleate, PEG Sorbitan Tetraoleate, PEG 400 Monoleate Polyoxyethylene monooleate, PEG-8 Oleate, PEG 400 Monostearate, PEG 400 Monostearate Polyoxyethylene monostearate Polyoxy-Ethylene Sucrose diester (Dierucat, PEG 35 Almond Glycerides, PEG 15 Glyceryl Isostearate, Polyoxyethylene alkyl phenol (Igepal Ca-630), PEG-35 castor oil (Cremophor EL/Cremophor EL-P BASF), Methyl-oxirane polymer with oxirane (Pluronic L-64 BASF), Polyoxyethylene alkyl ether (EMULGEN 707-EMULGEN MS-110-EMULGEN 709-EMULGEN LS-110-EMULGEN 1108-EMULGEN LS-114-EMULGEN 1118S-70-EMULGEN 1135S-70-EMULGEN 1150S-60), Polyglyceryl-3 Methyglucose Distearate=12 Oleth-10 Oleth-10/Polyoxyl 10 Oleyl Ether NF/ (PEG 10 Oleyl Ether), PEG 8 Isooctylphenyl Ether, PEG 10 Stearyl Ether, PEG 35 Castor Oil, Polyethylene glycol 400 monolaurate, Polyoxyethylene distyrenated phenyl ether (EMULGEN A-60-EMULGEN A-90-EMULGEN A-500), PEG 10 Cetyl Ether, PEG 40 Castor Oil, PEG-8 Laurate, Acconon C-50 (PEG-32 Hydrogenated Palm Glycerides/EP/ NF Stearoyl Macrogolglycerides (EP)/Stearoyl Polyoxylglycerides (NF)/Stearoyl polyoxyl-32 glycerides, PEG-35 hydrogenated castor oil (Cremophor RH40 BASF), PEG-40 hydrogenated castor oil (Cremophor RH40 BASF), PEG-1000 succinate(tocophersolan, D-α-tocopheryl/TPGS—Eastman), Polyoxyl-40-hydrogenated castor oil (Cremophor RH 40 BASF), Polyoxyethylene hydrogenated castor oil 40 (HCO-40 Nikkol), PEG 400 Monoluarate (Polyoxyethylene monolaurate), Polyoxyethylene sorbitan mono-oleate (Tween 80), Polyoxyethylene derivatives (EMULGEN B-66), PEG 10 Isooctylphenyl Ether, Polyoxyethylene cetyl ether (EMULGEN 220), Polysorbate 60 PE(20) sorbitan monostearate, PEG 12 Tridecyl Ether, PEG 18 Tridecyl Ether, PEG 40 Hydrogenated Castor Oil, Acconon C-44 (polyoxyethylene 32 lauric glycerides/PEG-32 Lauric Glycerides/Lauroyl Macrogolglycerides (EP)/Lauroyl Polyoxylglycerides (NF)/Lauroyl Polyoxyl-32 glycerides, PEG-60 hydrogenated castor oil (HCO-60-Nikko), PEG-8 caprylic/ capric glycerides (Labrasol-Gattefosse), Polysorbate 60 NF, Poloxyethylene sorbitan monostearate, Polysorbate 60, PEG-60 Almond Glycerides, PEG 20 Glyceryl Stearate, PEG 20 Stearate, PEG-20 Methyl Glucose Sesquistearate, Polysorbate 80, PEG-20 sorbitan monooleate (Tween-80 Atlas/ICI), Polyoxyethylene sorbitan monooleate, Polisorbate 60 (PS 60), Polyoxyethylene sorbitan monolaurate (Tween 20), Polysorbate 80, PEG 20 Stearyl Ether, PEG 20 Oleyl Ether, Polysorbate 80 PE(20) sorbitan monooleate, PEG 20 Cetyl Ether, PEG (20) Hexadecyl Ether, PEG 60 Hydrogenated Castor Oil, PEG 30 Stearate, PEG 75 Lanolin, Polysorbate 20, Polysorbate 20 NF, Polyoxyethylene lauryl ether (Brij 35), Polysorbate 20, Eumulgin® L (PPG-1-PEG-9 Lauryl Glycol Ether/Glycols, 1,2-, C12-16, ethoxylated propoxylated), PEG 23 Lauryl Ether, PEG-20 sorbitan monolaurate (Tween20 Atlas/ICI), Polyoxy-Ethylene Sucrose diester Dimyristate, PEG 40 Stearate, Polyoxy-Ethylene Sucrose diester Dinnyristate, Polyoxy-Ethylene Sucrose diester Dipalmitate, PEG 50 Stearate, PEG 40 Isooctylphenyl Ether, Polyoxy-Ethylene Sucrose diester Dioleate, Polyoxyethylene-polyoxypropylene copolymers (Pluronic F 127-BASF), PEG 100 Stearate, Polyoxyethylene myristyl ether (EMULGEN 4085), PEG-80 Sorbitan Laurate Linoleamide DEA, Stearamide MEA, Cetearyl Glucoside, Triethanolamine oleate, Sucrose monostearate, Oleth-10/ Polyoxyl 10 Oleyl Ether NF, Steareth-10, Ceteth-10, Cocamide MEA, Isosteareth-20, Sucrose laurate, Sucrose stearate, Lauramide DEA, Stearic Acid, Ceteareth-20, Oleth-20, Steareth-20, Steareth-21, Cetearyl Alcohol, Ceteth-20, Isoceteth-20, Ceteth-20, Sucrose palmitate, Laureth-23, Sodium oleate 16.9, Potassium oleate, Steareth-100, Sodium stearoyl-2-lactylate, Sodium stearoyl lactylate and a combination thereof.

The emulsifier is preferably selected from the group consisting of polyoxethylene derivatives, sorbitan esters, polyethylene glycol derivatives and a combination thereof.

Polyoxethylene can be polyoxyglycerides such as stearoyl polyoxyl-32 glycerides, lauroyl polyoxyl-32 glycerides or polyoxy-ethylene sucrose diester dimyristate, Polyoxy-ethylene sucrose diester dinnyristate, polyoxy-ethylene sucrose diester dipalmitate, polyoxy-ethylene sucrose diester dioleate; sorbitan esters can be polysorbate 80, polysorbate 60, polysorbate 20; polyethylene glycol derivatives can be PEG-8 laurate, PEG 400 monoluarate, PEG 10 isooctylphenyl ether, PEG 40 stearate, PEG 50 stearate, PEG 40 isooctylphenyl ether, and others selected from sodium stearoyl-2-lactylate, sodium stearoyl lactylate. The emulsifier is preferably polyoxylglycerides or polysorbates; and more preferably polyoxylglycerides. Thus, the emulsifier used in the present composition is preferably; polysorbate 80, polysorbate 60, polysorbate 20, stearoyl polyoxyl-32 glyceride (Acconon C-50/Gelucire 50/13) or lauroyl polyoxyl-32 glyceride (Acconon C-44/Gelucire 44/14).

In the prior art, it has been observed that the absorption and solubility of cannabinoid can be hindered due to CD binding to the free drug and thus reducing its free concentration according to Upadye et al. (AAPS PharmaSciTech 2010 June, 11(2) 509-517).

Whilst trying to solve the issue of CD binding to CBD and reducing its free concentration, it was discovered that the addition of an emulsifier with a specific HLB value, significantly ameliorated this issue, especially with the further addition of a silica derivative, preferably one with a high surface area and high tamped density. Which created a surprising synergy with the other two excipients as far as solubility and bioavailability of the cannabinoid is concerned, meanwhile providing excellent stability.

According to the present invention, the composition may further comprise at least one dextrin compound in an amount from 1 to 200 mg, preferably 1 to 150 mg and more preferably 1 to 100 mg, most preferably 4 to 75 mg per oral unit dose.

Dextrins are a group of low-molecular-weight carbohydrates produced by the hydrolysis of starch or glycogen. One preferred type of dextrin of the present invention is maltodextrin and the others are cyclodextrins.

Maltodextrin is a short-chain starch sugar used as a food additive in prior art. It is produced also by enzymatic hydrolysis from gelled starch and is usually found as a creamy-white hygroscopic spray-dried powder. Maltodextrin is easily digestible, being absorbed as rapidly as glucose, and might either be moderately sweet or have hardly any flavor at all.

The cyclical dextrins are known as cyclodextrins. They are formed by enzymatic degradation of starch by certain bacteria, for example, *Paenibacillus macerans (Bacillus macerans)*. Cyclodextrins have toroidal structures formed by 6-8 glucose residues.

The preferred dextrin compounds of the present invention are selected from the group consisting of beta cyclodextrin and derivatives including but not limited to: β-cyclodextrin, 2-hydroxypropyl-β-cyclodextrin, sulfobutylether β-cyclodextrin sodium salt, randomly methylated β-cyclodextrin, branched β-cyclodextrin and maltodextrin.

Although y-cyclodextrin compounds can also be employed, the preferred embodiment of the invention entails the use of beta cyclodextrins including; beta cyclodextrin (BCD), DM-β-cyclodextrin, RM-β-cyclodextrin and hydroxypropyl β-cyclodextrin (HPBCD), which have enhanced the solubility of cannabinoid even with the least expensive cyclodextrin compound β-cyclodextrin. In addition, formulations in the prior art have focused on extremely high ratios of cyclodextrin compounds such as HPBCD, contrary to the findings of the present invention that provides significantly higher levels of solubility with lower amounts of cyclodextrin compared to state of the art, when combined with emulsifiers that have a high HLB value.

Although substantially higher levels of solubility compared to marketed products containing either only an emulsifier or only an acid component can be achieved with the composition of the present invention. it has also been surprisingly discovered that the addition of a dextrin compound also favorably affects the solubility and bioavailability of the composition.

Although newer and significantly more expensive dextrin compounds such as DM-β-cyclodextrin and RM-β-cyclodextrin can also be employed within the compositions of the present invention, it has been surprisingly found that the composition of the present invention has enhanced the solubility of cannabinoid even with the least expensive dextrin compound. β-cyclodextrin provides a better solubility compared to the compositions found in the prior art which have employed methylated dextrin compounds. In addition, formulations in the prior art have focused on extremely low amounts of dextrin compounds such as DM-β-cyclodextrin at different ratios with the cannabinoid compound, contrary to the findings of the present invention that provides significantly higher levels of solubility with higher amounts of cyclodextrin compared to state of the art, when combined with emulsifiers that have a high HLB value and silica derivatives at specific ratios.

Although substantially higher levels of solubility compared to prior art containing either only an emulsifier or only a dextrin compound can be achieved with the composition of the present invention comprising a dextrin compound and an emulsifier; it has also been surprisingly discovered that polyoxyethylene derivatives and preferably sorbitan esters can have an even stronger effect on the solubility of cannabinoid compounds when combined with a cyclodextrin. The amphiphilic nature of sorbitan esters, combined with their high HLB value, coupled with the hydrophilic nature of the dextrins, combined with a silica derivative (preferably hydrophilic) results in this synergistic composition with a highly soluble and bioavailable cannabinoid inclusion complex that is also stable.

As most emulsifiers fit for use in the present invention are in liquid or semi liquid form, this creates a problem to be resolved, in order to manufacture solid cannabinoid compositions. If the compositions of the present invention have to be formulated in solid form when employing a liquid or semi liquid emulsifier such as Tween 80, silica derivatives are the preferred excipient(s). Silica derivatives have been used in oral dosage formulations for decades, there are many different silica derivatives used for various applications (i.e: to increase flowability, compressibility etc.) It has been surprisingly discovered that the use of silica derivatives does not have any negative impact and can even have a positive effect on the bioavailability of cannabinoids, as evidenced by the pharmacokinetic profile of composition 4 in the animal study detailed below.

The preferred silica derivatives of the present invention have an extremely low bulk density and high surface area. These silica derivatives have a mean particle diameter of 10 to 250 micron (determined according to the laser diffraction method) and a BET surface area of 40 to 400 m2/g (determined according to DIN 66 131 with nitrogen). The silica derivatives also typically have a pore volume of about 0.5 to 2.5 mL/g, wherein less than about 5% of the overall pore volume has a pore diameter of less than about 5 nm, the remainder being mesopores and macropores. Additionally, the silica derivatives typically will have a pH in the range of about 3.4 to about 8, preferably have a tamped (tapped) density of about 50 to 600 g/L and most preferably a tamped density between 50 to 400 g/L and are most preferably hydrophilic. (The tapped density is calculated according to ISO 787-11 and converted to the value in g/L)

As used herein, BET surface area means the surface area of a solid in relation to its mass, measured in $m^2/g$. As defined in DIN 66131, it is generally measured based on the BET method (Brunauer, Emmett, Teller, in Journal of the American Chemical Society 60 (1938), p. 309).

As used herein, tamped (tapped) density means a measured variable that describes the amount of volume lost by a powdered solid when it is shaken or packed down firmly as defined by ISO 787-11.

The silica derivative of the present invention is preferably selected as calcium silicate (such as Zeopharm) most preferably zeopharm 5170, or magnesium aluminometasilicate (such as Neusillin) most preferably Neusillin US2, or colloidal silicon dioxide, most preferably AEROPERL® 300.

The specific silica material that was used in the studies of the invention for compositions and methods was AEROPERL® 300 (a hydrophilic silica derivative), which is available from Evonik Degussa AG, Dusseldorf, Germany. However, other silica derivatives that have similar physical and chemical properties described herein can also be used.

In one embodiment of the invention, the particles of the silica derivative have a mean grain (particle) diameter of 10-120 micron. According to the present invention, particles of silica derivatives have a BET surface area of at least 150 m2/g, 200 m2/g, 250 m2/g or 275 m2/g.

According to the present invention, the oral composition formulated with the composition of the present invention can be solid, semi-solid or liquid form. Another advantage of the present invention is that the compositions can be in solid form (powder form). In the prior art, solid form of cannabinoid formulation has significant limitation on the solubility and bioavailability therefore its products on the market, especially ones claiming the highest bioavailability and solubility, are generally in oil or liquid form. Although higher amounts of an emulsifier can be employed within the composition of the present invention, the use of high amounts (higher than 75% by volume) of high HLB value emulsifiers is not preferable because it has been found that emulsifiers can impair the function of the mucosal barrier and increases the permeability of the gut especially at high doses. Although this would increase the permeability of a cannabinoid from the intestinal mucosal barrier, it will also damage the mucosal barrier itself, especially with long term use and lead to other secondary complications.

According to the present invention, the composition comprises cannabinoid compound in an amount of 5% to 60%, preferably 5% to 50%, more preferably 5% to 40% and most preferably 5% to 30% by the weight of the composition.

According to the present invention, the composition comprises at least one emulsifier in an amount of between 20 to 90%, preferably 30 to 90% and more preferably 40 to 90% by the weight of the composition.

According to the present invention, the composition comprises at least one silica derivative (when in solid or semi-solid form) in an amount of between 1 to 70%, preferably 10 to 60% and more preferably 20 to 60% by the weight of the composition.

According to the present invention, the composition comprises at least one dextrin compound in an amount of between 1 to 50%, preferably 2 to 25% and more preferably 2 to 15% by the weight of the composition.

For the avoidance of doubt; the term "weight of the composition" used in the calculations means the sum of the weight of the compound with cannabinoid content, the weight of the emulsifier, the weight of the acid component, and optionally the weight of the dextrin compound and the weight of the silica derivative.

According to the present invention, the dextrin compound: emulsifier ratio is between 0.5:1 to 1:25, and preferably between 1:1 to 1:20 more preferably between 1:2 to 1:15, most preferably between 1:4 to 1:15. and the ratio of the emulsifier to the silica derivative is between 3:1 to 1:2, and preferably 2:1 to 1:2, more preferably between 1:1 to 2:1. As the specific combination of the emulsifier with the acid component provides improved solubility of cannabinoid, their weight ratio is very important. Thus the ratio of the emulsifier to the acid component is between 40:1 to 20:1. and preferably 30:1 to 20:1 and most preferably 30:1 to 15:1. The correct ratio enables the composition to reach to the needed solubility and bioavailability of cannabinoid. Especially when a dextrin compound and silica derivative is added. Accordingly, a 100 times higher bioavailability is achieved by the present invention compared to the singular use of a cannabinoid compound (i.e.: cannabidiol, THC, THCV).

Moreover, it has been found that the stability of the composition of the present invention is excellent at room temperatures (25° C.±2° C./40% RH±5%) with air tight packaging, up to a period of 12 months, wherein the CBD content of the composition were no less than 90% compared with day "0".

According to the present invention, the ratio of the cannabinoid compound to the dextrin compound is between 1:0.1 to 2:1, preferably 1:0.1 to 1:1.

The most preferred embodiment of the present invention has a ratio of the compound with cannabinoid content (cannabinoid compound) to emulsifier is between 1:3 to 1:9 and the ratio of the compound with cannabinoid content to the acid component is between 10:1 to 1:1, preferably between 5:1 to 1:1, the ratio of the compound with cannabinoid content to the dextrin compound is between 5:1 to 1:1 and the ratio of the cannabinoid compound with the silica derivative is between 1:2 to 1:8.

Due to the lower amounts of dextrin compound and especially lower amount of acid component used within the composition, a higher amount of a cannabinoid per unit dose can be employed within the formulation, which is of great importance; because the size of the dosage form can be decreased in this manner or the amount of cannabinoid per unit dose can be increased compared to the prior art, especially with the high amount of loading that can be done with specific types of silica derivatives.

Accordingly, the present invention provides an oral composition comprising a cannabinoid compound, a silica derivative, a dextrin compound and at least one emulsifier selected from the group consisting of sorbitan esters (polysorbates), polyoxyglycerides and a combination thereof.

In another embodiment, the cannabinoid compound has at least 5% cannabinoid content, preferably at least 10% cannabinoid content, more preferably at least 20% cannabinoid content, and most preferably over 30% cannabinoid content.

In a preferred embodiment the cannabinoid is selected as CBD, THC or THCV. Therefore, the CBD, THC or THCV content within the cannabinoid compound is preferably between 10% to 99%

For the avoidance of doubt; the term "per oral unit dose" means: the weight of the cannabinoid compound or the weight of the dextrin compound or the weight of the silica derivative or the weight of the emulsifier within a single administration, such as a single tablet, a single capsule, or the amount of drops that would be described in a patient information leaflet as the amount of the cannabinoid that would be taken by the patient (e.g; 5 puffs of an oral spray or 20 drops of a solution) taken at a single time. As for food and beverages, the single unit dose would be equal to the serving size of a beverage or food product (e.g; if a cannabinoid containing cake is 500 grams but a single serving is written on the label as 100 grams, the single unit dose would be 100 grams) The same principle would be applied to beverages.

The oral unit dosage forms prepared with the composition of the present invention can be administered 1 to 6 times daily and usually will not need to be administered more than 6 times due to the superior solubility and significant bioavailability that can be attained.

The oral dosage forms prepared with the compositions of the present invention can be used for the treatment or prophylaxis of a variety of diseases and/or medical conditions. In some embodiments, the diseases include, but are not limited to, Acquired Hypothyroidism, Acute Gastritis, Acute Pain, Agoraphobia, AIDS Related Illness, Alcohol Abuse, Alcoholism, Alopecia Areata, Alzheimer's Disease, Amphetamine Dependency, Amyloidosis, Amyotrophic Lateral Sclerosis (ALS), Angina Pectoris, Ankylosis, Anorexia, Anorexia Nervosa, Anxiety Disorders, any chronic medical symptom that limits major life activities, any Chronic Medical Symptom that Limits Major Life Activities, Arteriosclerotic Heart Disease, Arthritis, Arthritis (Rheumatoid), Arthropathy, gout, Asthma, Attention Deficit Hyperactivity Disorder (ADD/ADHD), Autism/Asperger's, Autoimmune Disease, Back Pain, Back Sprain, Bell's Palsy, Bipolar Disorder, Brain Tumor, Breakthrough Pain, Malignant, Bruxism, Bulimia, Cachexia, Cancer, Carpal Tunnel Syndrome, Cerebral Palsy, Cervical Disk Disease, Cervicobrachial Syndrome, Chemotherapy Chronic Fatigue Syndrome, Chronic Pain, Chronic renal failure, Cocaine Dependence, Colitis, Conjunctivitis, Constipation, Crohn's Disease, Cystic Fibrosis, Damage to Spinal Cord Nervous Tissue, Darier's Disease, Degenerative Arthritis, Degenerative Arthropathy, Delirium Tremens, Dermatomyositis, Diabetes, Diabetic Neuropathy, Diabetic Peripheral Vascular Disease, Diarrhea, Diverticulitis, Dysthymic Disorder, Eczema, Emphysema, Emphysema, Endometriosis, Epidermolysis Bullosa, Epididymitis, Epilepsy, Felty's Syndrome, Fibromyalgia, Friedreich's Ataxia, Gastritis, Genital Herpes, Glaucoma, Glioblastoma Multiforme, Graves Disease, Cluster Headaches, Migraine Headaches, Tension Headaches, Hemophilia A, Henoch-Schonlein Purpura, Hepatitis C, Hereditary Spinal Ataxia, HIV/AIDS, Hospice Patients, Huntington's Disease, Hypertension, Hypertension, Hyperventilation, Hypoglycemia, Impotence, Inflammatory autoimmune-mediated arthritis, Inflammatory Bowel Disease (IBD), Insomnia, Intermittent Explosive Disorder (IED), Intractable Pain, Intractable Vomiting, Lipomatosis, Lou Gehrig's Disease, Lyme Disease, Lymphoma, Major Depression, General Anxiety Disorder, Malignant Melanoma, Mania, Melorheostosis, Meniere's Disease, Motion Sickness, Mucopolysaccharidosis (MPS), Multiple Sclerosis (MS), Muscle Spasms, Muscular Dystrophy, Myeloid Leukemia, Nail-Patella Syndrome, Nightmares, Obesity, Obsessive Compulsive Disorder, Opiate Dependence, Osteoarthritis, Panic Disorder, Parkinson's Disease, Peripheral Neuropathy, Peritoneal Pain, Persistent Insomnia, Porphyria, Post Polio Syndrome (PPS), Post-traumatic arthritis, Post-Traumatic Stress Disorder (PTSD), Premenstrual Syndrome (PMS), Prostatitis, Psoriasis, Pulmonary Fibrosis, Quadriplegia, Radiation Therapy, Raynaud's Disease, Reiter's Syndrome, Restless Legs Syndrome (RLS), Rheumatoid Arthritis, Rheumatoid Arthritis, Rheumatoid Arthritis, Rosacea, Schizoaffective Disorder, Schizophrenia, Scoliosis, Sedative Dependence, Seizures, Senile Dementia, Severe Nausea, Shingles (Herpes Zoster), Sinusitis, Skeletal Muscular Spasticity, Sleep Apnea, Sleep Disorders, Spasticity, Spinal Stenosis, Sturge-Weber Syndrome (SWS), Stuttering, Tardive Dyskinesia (TD), Temporomandibular joint disorder (TMJ), Tenosynovitis, Terminal Illness, Thyroiditis, Tic Douloureux, Tietze's Syndrome, Tinnitus, Tobacco Dependence, Tourette's Syndrome, Trichotillomania, Viral Hepatitis, Wasting Syndrome, Whiplash, Wittmaack-Ekbom's Syndrome, Writers' Cramp, nausea, vomiting, premenstrual syndrome, unintentional weight loss, insomnia, and lack of appetite, spasticity, painful conditions, especially neurogenic pain, movement disorders, asthma, glaucoma, adrenal disease, inflammatory bowel disease, migraines, fibromyalgia, and related conditions, multiple sclerosis, spinal cord injuries. It exhibits antispasmodic and muscle-relaxant properties as well as stimulates appetite. Other studies state that cannabis or cannabinoids may be useful in treating alcohol abuse, amyotrophic lateral sclerosis, collagen-induced arthritis, asthma, atherosclerosis, bipolar disorder, colorectal cancer, HIV-Associated Sensory Neuropathy, depression, dystonia, epilepsy, digestive diseases, gliomas, hepatitis C, Huntington's disease, leukemia, skin tumors, methicillin-resistant Staphylococcus aureus (MRSA), Parkinson's disease, pruritus, posttraumatic stress disorder (PTSD), psoriasis, sickle-cell disease, sleep apnea, and anorexia nervosa, drug dependence, moderate to severe pain management, insomnia, anxiety, epilepsy, seizures, parkinson's and also for the treatment of various cancers including blood cancers and solid tumors.

In another embodiment of the present invention, the use of the composition in oral dosage forms, further comprises at least one other acceptable excipient as a carrier.

Oral dosage forms of the present invention may comprise other excipients such as: suitable diluents, binders, lubricants, preservatives, antioxidants, flavoring agents, disintegrating agents, surfactants, glidants, sweetening agents, coloring agents and coating agents as pharmaceutically acceptable excipients and preferably disintegrant, lubricant and mixture thereof.

Moreover, due to the composition of this invention, quality, such as the external appearance, bitter taste, aftertaste, is improved, even without the addition of extra sweeteners and flavoring agents. This aspect of the invention is especially important for manufacturing food and beverages with cannabinoid content.

Oral dosage forms of the present invention may be tablet, capsule, gel capsule, pellet, granule, hard gelatine capsule, sachet in powder, liquid form, tablet in tablet, tablet in capsule, powder or coated tablet, preferably being tablet or capsule. The oral dosage forms may also be in the form of drop, pellet, granule, solution, suspension, syrup, powder, preferably made for sublingual or oromucosal application in the form of drops, sublingual tablets, sprays, strips or as a chewing gum.

Acceptable diluents of the present invention may be selected from magnesium stearate, lactose, microcrystalline cellulose, starch, pre-gelatinized starch, calcium phosphate, calcium sulphate, calcium carbonate, sodium starch glycolate, mannitol, sorbitol, xylitol, sucrose, maltose, fructose, dextrose and the like or mixtures thereof.

Acceptable binders of the invention may be selected from starches, natural sugars, corn sweeteners, natural and synthetic gums, cellulose derivatives, gelatin, polyvinylpyrrolidone, polyethylene glycol, waxes, sodium alginate, alcohols, water and the like or mixtures thereof.

Acceptable lubricants of the present invention may be selected from metallic stearates, metallic lauryl sulfates, fatty acids, fatty acid esters, fatty alcohols, paraffins, hydrogenated vegetable oils, polyethylene glycols, boric acid, polyvinylpyrrolidone, sodium benzoate, sodium acetate, sodium chloride, talk and the like or mixtures thereof.

Acceptable disintegrating agents of the present invention may be selected from starches, cellulose derivatives, polyvinylpyrrolidone, crospovidone, clays, ion-exchange resins, alginic acid, sodium alginate and the like or mixtures thereof.

Flavoring agent(s) that may be used in the invention is meant to impart a pleasant flavor and/or odor to the oral composition. Suitable flavoring agents include but not limited to natural and artificial flavors, such as synthetic flavor oils and flavoring aromatics and/or natural oils, extracts from plants, leaves, flowers, fruits and so forth and combinations thereof. Representative suitable flavoring agents may be for example, without limitation, menthol, cinnamon, wintergreen, clove, bay, anise, eucalyptus, thyme, cedar leave, nutmeg, sage, bitter almonds and cassia, vanilla, artificial vanilla, chocolate, artificial chocolate, bubble gum, both natural and artificial fruit flavors, such as cherry flavor, grape flavor, orange flavor, banana flavor, strawberry flavor, lemon flavor, grapefruit flavor and "mint" flavors such as peppermint flavor and spearmint flavor, lime flavor, apple flavor, pear flavor, peach flavor, raspberry flavor, plum flavor, pineapple flavor, apricot flavor and so forth, including combinations of two or more thereof. Flavoring agents are generally provided as a minor component of the composition in amounts effective to provide a palatable flavor to the composition. The amount of flavoring agent may depend on a number of factors, including the desired organoleptic effect. The precise amount of sweetening and/or flavoring agent(s) depends on the properties of the agent(s) used, however generally in an amount that is sufficient to mask the unpleasant taste and/or odor associated with cannabinoids as determinable by one skilled in the art. However, flavoring agents generally present is in a pharmaceutically or nutraceutically acceptable range.

Sweeteners suitable for inclusion in the present invention may be determined by one skilled in the art including, for example without limitation, both natural and artificial sweeteners such as the representative sweetening agents of intense sweeteners such as sorbitol, sucrose, saccharine such as sodium saccharin, cyclamates such as sodium cyclamates, aspartame, sucralose, thaumatin, acesulfam K, and the like, and sugars such as monosaccharides, disaccharides and polysaccharides. Representative sugars useful in the present invention include, without limitation, xylose, ribose, glucose, mannose, galactose, fructose, dextrose, sucrose, maltose, partially hydrolyzed starch or corn syrup, and sugar alcohols such as sorbitol, xylitol, mannitol, glycerin, etc. and combination thereof. Presently preferred as a sugar sweetener is sucralose. Sugar sweeteners may be replaced or augmented by water-soluble artificial sweeteners, such as the suitable artificial sweeteners previously listed and mixtures thereof. The amount of artificial sweetener used in the composition may vary to provide an appropriate amount of sweetness as determinable by one skilled in the art. Mixtures of sweetening and/or flavoring agents are preferably used.

Examples of preservatives suitable for use in the present invention include, for example without limitation, one or more alkyl hydroxybenzoates, such as methyl hydroxybenzoates, ethyl hydroxybenzoates, propyl hydroxybenzoates, butyl hydroxybenzoates and the like.

Additional preservatives useful in the present invention include, but are not limited to, sodium benzoate, potassium sorbate, salts of edetate (also known as salts of ethylenediaminetetraacetic acid, or EDTA, such as disodium edetate), pimaricin based preservatives and antimicrobial agents including parabens (p-hydroxybenzoic acids esters) such as methyl paraben, ethylparaben, propylparaben, butylparaben and the like, and combinations thereof. although other pharmaceutically acceptable preservatives may be substituted, therefore. Preservative(s) as used in the composition are in an acceptable range.

The composition may also contain a viscosity enhancing agent(s) which include but are not limited to gums; sorbitol; glycerol; polyvinyl alcohol; polyvinyl pyrrolidone; polyethylene oxide; cellulose derivatives, such as hydroxypropylmethylcellulose or a salt thereof, alkyl ether of cellulose, such as methylcellulose, ethylcellulose, hydroxyethylcellulose, hydroxyethylmethylcellose and mixtures thereof. Preferably the viscosity-enhancing agent is hydroxypropylmethylcellulose e.g. (HPMC K4M, HPMC K100 LVP; HPMC K15 MP; HPMC E4 MP; HPMC E10 MP CR).

The composition may also contain a pH-stabilizing agent to maintain a desired pH. The term "pH-stabilizing agent" encompasses buffers and pH-altering agents. Suitable pH-stabilizing agents include but not limited to tribasic sodium phosphate, anhydrous sodium carbonate, glycine, citric acid or mixtures thereof.

Preferably the pH of the composition is in range of about 3 to about 7.5.

Most preferably the pH of composition is in range from about 5 to about 7.5

Although it has been previously shown that CBD degrades under acidic conditions. It has surprisingly been found with the composition of the present invention that neutral to slightly more acidic conditions create a more stable liquid cannabinoid formulation and as such, it is preferable to have a pH that is neutral or slightly acidic, especially when the formulation is in liquid form. (Merrick et. Al, Cannabis Cannabinoid Res. (2016), 1(1), 102-112) Hence the surprising effect of the acid component becomes 2-fold due to the added benefit of increased stability.

The composition may also contain antioxidant(s) preferably selected as tocopherols, gallic acid and gallates, isomaltulose, butylated hydroxy anisole, butylated hydroxy toluene, ascorbic acid, maleic acid, sodium bisulphate, sodium metabisulphite, sodium formaldehyde sulphoxylate and the like.

In a preferred embodiment, when the composition of the present invention is used in a unit dose formulation, the pH—stabilizing agent(s), antioxidant(s), preservative(s) may be included in the manufacturing of the finished dosage formulation to be used by the end consumer/patient, to increase shelf life of the final product; they may be included from about 0.001% to about 20% of the tablet, capsule, beverage or food product based on the total weight of a single unit dose or single serving size.

The most preferred emulsifiers of the present invention such as polysorbate 80, polysorbate 60, polysorbate 20 are all available both as nutraceutically and pharmaceutically acceptable excipients providing flexibility for commercializing/registering the compositions of the present invention. The same advantage is also attained with most cyclodextrins, especially beta cyclodextrin which is also pharmaceutically and nutraceutically acceptable excipients. And silica derivatives, such as colloidal silicon dioxide are also a pharmaceutically and nutraceutically acceptable excipient. Therefore, the composition of the present invention is developed for use as a medicinal product and/or supplement(s) and/or as beverages or food products.

In another embodiment, the present invention provides oral dosage forms that can be prepared with the composition such as a nutraceutical composition, pharmaceutical composition, beverages or food products (such as nutraceutical bars, cakes, chocolate bars, cookies, ice cream, cereals).

It has also been observed by the inventor that the particle size of the cannabinoid compound has a significant effect on the transparency of the liquid when the composition of the present invention is mixed with water or used in beverages, thus in a preferred embodiment; if the composition of the present invention is to be used in the manufacturing of liquid dosage forms, at least 40% of the particles will have a particle size between 5 and 100 microns and most preferably between 5 and 20 microns as this creates a clearer liquid solution. The particle size of the cannabinoid compound is calculated with the Malvern Mastersizer 3000E. The desired particle size is attained through micronisation. The micronisation can also be done prior to mixing the cannabinoid compound with the excipients according to the present invention to decrease the total weight of the composition to be micronized. Which would be economically more feasible.

In another embodiment, the present invention provides a manufacturing method to obtain the oral composition comprising the step of mixing a cannabinoid compound, at least one emulsifier, and at least one acid component, for at least 10 minutes.

In another embodiment, the present invention provides a manufacturing method to obtain the oral composition comprising the step of mixing a cannabinoid compound, at least one emulsifier, and at least one acid component, and at least one dextrin compound for at least 10 minutes.

In another embodiment, the present invention provides a manufacturing method to obtain the oral composition comprising the step of mixing a cannabinoid compound, at least one emulsifier, at least one acid component, at least one dextrin compound and at least one silica derivative for at least 10 minutes.

The method according to the present invention comprises the step of mixing firstly the cannabinoid compound with the emulsifier and/or dextrin compound, before mixing with the silica derivative.

The mixing can also be performed using a conventional cubic mixer, tumbler, fluid bed dryer or spray dryer depending on the process and the form of excipients employed. The mixing is preferably performed with a high sheer mixer or fluid bed dryer (especially if agglomeration is a desired outcome) The high sheer mixer or fluid bed dryer can also be equipped with a spray nozzle.

The method according to the present invention preferably comprises the steps of mixing firstly at least one cannabinoid compound with at least one emulsifier, and then mixing with at least one dextrin compound and optionally with at least one silica derivative.

The method according to the present invention comprises the steps of:
    a. Mixing the cannabinoid compound and emulsifier under room temperature with a high shear mixer,
    b. Adding the organic acid.

In a preferred embodiment the method according to the present invention comprises the steps of:
    a. Mixing the cannabinoid compound and emulsifier under room temperature with a high shear mixer,
    b. Adding the dextrin compound and the organic acid,
    c. Mixing the mixture of step b) with the silica derivative until the mixture turns into powder form,
    d. Sieving the powder mixture through a 200 μm to 2000 μm sieve.

The method according to the present invention preferably comprises the steps of:
    1. Mixing the cannabinoid compound and emulsifier under room temperature with high sheer mixer at 300 rpm for 25 minutes,
    2. Adding the organic acid and continue mixing for 10 minutes at 300 rpm,
    3. Adding the silica derivative after bringing the mixer's speed down to 50 rpm until the mixture turns into powder form,
    4. Sieve the powder mixture from step 3 with a 500 μm stainless steel sieve.

The method according to the present invention most preferably comprises the steps of:
1. Mixing the cannabinoid compound and emulsifier under room temperature with high sheer mixer at 300 rpm for 25 minutes,
    2. Adding the dextrin compound and organic acid and continue mixing for 10 minutes at 300 rpm,
    3. Adding the silica derivative after bringing the mixer's speed down to 50 rpm until the mixture turns into powder form,
    4. Sieve the powder mixture from step 3 with a 500 μm stainless steel sieve.

Unless otherwise defined, all technical and scientific terms used herein have the same meaning as commonly understood by one of ordinary skill in the art. In addition, the materials, methods, and examples are illustrative only and not intended to be limiting.

The invention now will be described in particularity with the following illustrative examples; however, the scope of the present invention is not intended to be, and shall not be, limited to the exemplified embodiments below.

Examples

Manufacturing Examples

The amount of the dextrin compound and emulsifier can be adjusted according to the desired dose of cannabinoid compound which is based on the cannabinoid content of the compound. For the purposes of obtaining accurate results about the effects of the compositions on the solubility of cannabinoid, a CBD isolate with 99.83% CBD content was used in the studies, Example 1

| Ingredient | Amount (g) |
|---|---|
| CBD | 5000 |
| β-cyclodextrin | 1250 |
| stearoyl polyoxyl-32 glyceride (Acconon C-50) | 15000 |
| Aeroperl 300 (colloidal silicon dioxide) | 1000 |
| Stearic acid | 2250 |

Manufacturing Process 1. 5000 grams of CBD, 1250 grams of beta-cyclodextrin and 2250 grams of stearic acid are weighed and mixed by using a cubic mixer at 80 rpm for 5 minutes.
2. 15000 grams of Acconon C-50 is weighed and grinded until Acconon C50 is in powder form.
3. Acconon C-50 is added along with Aeroperl 300 to the mixed powder in step 1 and mixed in the cubic mixer at 80 rpm for 15 min.
4. Mixed powder is passed through a 0.5-mm sieve.

Example 2

| Ingredient | Amount (g) |
|---|---|
| CBD | 5000 |
| Maltodextrin | 3500 |
| Polysorbate 80 | 30000 |
| Colloidal silicon dioxide (Aeroperl 300) | 22500 |
| Stearic Acid | 2250 |

Manufacturing Process 1. 5000 grams of CBD and 30.000 grams of polysorbate 80 is weighed and mixed in a high sheer mixer at 300 rpm for 25 minutes.
2. 3500 grams of maltodextrin and 2250 grams of stearic acid is weighed and added into the mixture described in step 1 and mixed for 15 minutes.
3. 22.500 grams of Aeroperl 300 is slowly added in 20-30 minutes (to prevent clumps) to the mixture in step 2, whilst mixing at 50 rpm.

4. The resulting powder from step 3 is sieved by 500 um stainless steel sieve.

Example 3 (Liquid Formulation)

| Ingredient | Amount (g) |
|---|---|
| CBD | 5000 |
| Maltodextrin | 3500 |
| Polysorbate 80 | 30000 |
| Stearic Acid | 2250 |

Manufacturing Process 1. 5000 grams of CBD and 30.000 grams of polysorbate 80 is weighed and mixed in a high sheer mixer at 300 rpm for 25 minutes.
2. 3500 grams of maltodextrin and 2250 grams of stearic acid is weighed and added into the mixture described in step 1 and mixed for 15 minutes.

Dissolution Tests

Dissolution Profiles of Selected Formulations Below

Dissolution study was performed in 900 ml volume with a USP type II apparatus at pH 6.8 phosphate buffer. HPLC analysis (as per below) was used to quantify the amount of CBD released at each time point.

| | | % CBD API Released | | | | | |
|---|---|---|---|---|---|---|---|
| n | Min | Formulation 1 | Formulation 2 | Formulation 3 | Formulation 4 | Formulation 5 | Formulation 6 |
| 1 | 5 | 0 | 0 | 1,13 | 0,76 | 38,56 | 42,83 |
| 2 | 10 | 0,59 | 8,35 | 4,5 | 2,34 | 35,1 | 36,48 |
| 3 | 15 | 0,67 | 8,01 | 4,79 | 4,67 | 24,78 | 38,3 |
| 4 | 30 | 3,56 | 9,57 | 4,42 | 9,43 | 27,1 | 38,82 |
| 5 | 60 | 15,18 | 9,8 | 6,62 | 8,74 | 28,42 | 45,41 |
| 6 | 120 | 25,08 | 8,07 | 7,56 | 10,82 | 23,12 | 31,24 |
| 7 | 180 | 32,67 | 8,32 | 7,94 | 11,31 | 20,34 | 25,29 |
| 8 | 240 | 33,08 | 9,15 | 8,66 | 12,04 | 24,05 | 36,11 |
| | | Contents | Contents | Contents | Contents | Contents | Contents |
| | | 50 mg Cannabidiol 50 mg Tween 80 | 50 mg Cannabidiol 15 mg maltodextrin | 50 mg Cannabidiol 25 mg Stearic Acid | 50 mg Cannabidiol 100 mg Tween 80 | 50 mg Cannabidiol 100 mg Tween 80 22,5 mg Stearic Acid | 50 mg Cannabidiol 31,25 mg BCD 100 mg Tween 80 75 mg Aeroperl 12,5 mg Stearic acid |

| | | | % CBD API Released | | | |
|---|---|---|---|---|---|---|---|
| n | Min | Formulation 7 | Formulation 8 | Formulation 9 | Formulation 10 | Formulation 11 | CBD API |
| 1 | 5 | 38,08 | 42,13 | 36,13 | 98,69 | 99,21 | 1,89 |
| 2 | 10 | 27,53 | 28,24 | 27,41 | 76,87 | 98,47 | 1,89 |
| 3 | 15 | 27,19 | 28,15 | 27,22 | 74,07 | 81,47 | 2,05 |
| 4 | 30 | 23,77 | 31,17 | 33,63 | 81,73 | 95,1 | 2 |
| 5 | 60 | 34,53 | 38,68 | 37,27 | 82,52 | 95,26 | 2,01 |
| 6 | 120 | 19,6 | 25,19 | 45,25 | 82,84 | 80,38 | 1,97 |
| 7 | 180 | 19,33 | 24,32 | 41,57 | 84,07 | 95,78 | 2,2 |
| 8 | 240 | 26,38 | 28,73 | 41,98 | 86,45 | 96,55 | 2,32 |
| | | Contents | Contents | Contents | Contents | Contents | Contents |
| | | 50 mg Cannabidiol 31,25 mg BCD 160 mg Tween 80 120 mg Aeroperl 12,5 mg Citric Acid | 50 mg Cannabidiol 31,25 mg BCD 160 mg Tween 80 120 mg Aeroperl 12,5 mg Stearic Acid | 50 mg Cannabidiol 35 mg Maltodextrin 160 mg Tween 80 120 mg Aeroperl 12,5 mg Stearic acid | 50 mg Cannabidiol 35 mg Maltodextrin 450 mg Tween 80 22,5 mg Stearic asit | 50 mg Cannabidiol 35 mg Maltodextrin 300 mg Tween 80 22,5 mg Stearic asit | 50 mg Cannabidiol |

HPLC Analysis

Method: High Performance Liquid Chromatography (HPLC); Shimadzu LC-2040 3D Nexera-i
Wave lenght: 220 nm
Column 100 mm*4.6 mm; 5 μm C18 (InertSustain)
Column Temperature: 25° C.
AutoSampler Temperature: 5° C.
Injection Volume: 5 μL
Flow rate: 1.0 mL/min
Mobile Phase: Methanol:Water (85:15 h/h)
Diluent: Methanol
Run Time: Cannabidiol=3.7 min Evaluation of the Results The highly synergistic effect of the composition of the present invention is demonstrated by the fact that the composition of an emulsifier which is polysorbate 80 (Formulation 1) with CBD has provided only about 15% API release at simulated intestinal fluid at 1 hour, and the composition of CBD with maltodextrin (Formulation 2) has provided about 10% API release at 1 hour. The composition of CBD with an acid component (Formulation 3) has provided about 6.6% API release at 1 hour. However, the combination mixture of both the acid component and emulsifier with CBD (Formulation 4) has provided about 28% of API release at 1 hour demonstrating a synergistic effect of the acid component and emulsifier rather than one additive. This proves a significant increase with the primary composition of the present invention with an emulsifier to CBD ratio of 2:1 and an acid component to CBD ratio of 1:2. Although, the addition of the dextrin compound had a significant effect as it can be seen with the release profile of formulation 5. The dissolution profile was significantly better when the ratio of the emulsifier was increased up to 6 times of CBD, and the ratio of the acid component to CBD was increased from 1:4 closer to 1:2. Stearic acid had better results when compared with citric acid but both components had a positive effect on the release profile of the CBD API, as it can be seen with formulations 6 and 7.

The difference between formulations 10 and 11 demonstrate that the increase of the emulsifier content above a certain threshold does not necessarily provide a better release profile but in fact has a minor negative impact.

Accordingly, the preferred embodiment of the present invention entails the use of an emulsifier, an acid component and a compound with cannabinoid content wherein the ratio of the compound with cannabinoid content to emulsifier is between 1:2 to 1:9 and the ratio of the compound with cannabinoid content to the acid component is between 10:2 to 10:7. The preferred embodiment of the present invention entails the use of an emulsifier, an acid component, a dextrin compound and a compound with cannabinoid content wherein the ratio of the compound with cannabinoid content to emulsifier is between 1:2 to 1:9, the ratio of the compound with cannabinoid content to the acid component is between 10:2 to 10:7 and the ratio of the compound with cannabinoid content to the dextrin compound is between 5:1 to 1:1

The most preferred agents used for making the compositions in solid form are silica derivatives as they have surprisingly been found to further improve the pharmacokinetic parameters of cannabinoids as evidenced by the PK study outlined below.

Animal Study (Pharmacokinetics)

According to the results of the dissolution study, compositions were prepared by adhering to the ratios of the present invention. Formulations 10 and 11 from the dissolution study were modified for the compositions of the pharmacokinetic study, since these 2 formulations had the superior results.

6 rats weighing 250+/−20 grams were used per each study group and a total of 5 groups were used. The compositions were administered by gavage at the human dose equivalent of 40 mg CBD per composition.

The results were analyzed by blood draws at each of the time points over an 8 hour period. An HPLC system was used to determine the blood concentration of CBD at the specified time points. The blood concentrations were given as (μg/mL)

The average CBD blood concentration of the groups were used to determine the pharmacokinetic parameters of Cmax, AUC and Tmax.

| Ingredients | Composition 1 in mg | Composition 2 in mg | Composition 3 in mg | Composition 4 in mg | CBD API in mg |
|---|---|---|---|---|---|
| CBD | 40 | 40 | 40 | 40 | 40 |
| Maltodextrin | | | 31.25 | 31.25 | |
| Tween 80 | 300 | 300 | 300 | 300 | |
| Stearic Acid | 7 | 22.5 | — | 22.5 | |
| Aeroperl | — | — | — | 222.04 | |
| Total Volume | 393.75 | 362.50 | 371.25 | 600.29 | |

Blood Concentrations of 5 Groups Given as (μg/mL) Over an 8-Hour Time Period.

| HOUR | Group 1 | Group 2 | Group 3 | Group 4 | Group 5 (CBD Alone) |
|---|---|---|---|---|---|
| 0 | 0.000 | 0.000 | 0.000 | 0.000 | 0.000 |
| 0.083 | 0.248 | 1.336 | 0.516 | 1.544 | 0.008 |
| 0.25 | 0.447 | 0.608 | 0.608 | 1.192 | 0.011 |
| 0.5 | 0.345 | 0.358 | 0.548 | 0.654 | 0.015 |
| 1 | 0.286 | 0.432 | 0.199 | 0.257 | 0.013 |
| 2 | 0.235 | 0.246 | 0.269 | 0.331 | 0.011 |
| 4 | 0.342 | 0.229 | 0.279 | 0.185 | 0.008 |
| 8 | 0.292 | 0.207 | 0.347 | 0.484 | 0.006 |

Pharmacokinetic Parameters

| | Cmax | Tmax/Hour | AUC(0-8 h) |
|---|---|---|---|
| Composition 1 | | | |
| | 0.447 | 0.25 | 2.429 |
| Comparison with API/Cmax Multiple | 29.79 | | |
| Comparison with API/AUC Multiple | | | 34.13 |
| Composition 2 | | | |
| | 1.336 | 0.083 | 2.223 |
| Comparison with API/Cmax Multiple | 89.09 | | |
| Comparison with API/AUC Multiple | | | 31.23 |
| Composition 3 | | | |
| | 0.608 | 0.25 | 2.480 |
| Comparison with API/Cmax Multiple | 40.51 | | |
| Comparison with API/AUC Multiple | | | 34.85 |
| Composition 4 | | | |
| | 1.544 | 0.083 | 2.901 |
| Comparison with API/Cmax Multiple | 102.94 | | |
| Comparison with API/AUC Multiple | | | 40.76 |
| CBD API | | | |
| | 0.015 | 0.50 | 0.071 |

Evaluation of the Results

The results clearly demonstrate that the compositions of the present invention with the ratios described in its embodiments and examples have a significant effect on the solubility and bioavailability of cannabinoids.

Compositions 2 and 4 stand out as they demonstrate a superior pharmacokinetic profile, in regards to all 3 parameters of Cmax, AUC, and Tmax.

Composition 4 increased the Cmax of CBD more than 100 times higher compared with CBD alone, decreased the Tmax to 5 minutes after administration. Compared with 30 minutes with the CBD API and increased the AUC to about 40 times higher than CBD alone. Thus enabling a significantly faster, stronger and longer lasting effect. All of which are important for the application of cannabinoid compounds.

Some examples of oral dosage formulations of CBD compositions where the compositions of the present invention can be used:

Example 8

| Nutraceutical or Pharmaceutical Capsule of CBD | |
|---|---|
| Ingredients | mg |
| CBD (%99.83)* | 50 |
| Polysorbate 80 | 300 |
| Maltodextrin | 35 |
| Stearic Acid | 22.5 |
| Aeroperl 300 | 225 |
| Magnessium stearate | 6.5 |
| Lactose monohydrate | 7.5 |
| Weight without capsule shell | 646.5 |
| Hard gelatin capsule | 130 |
| Total weight with capsule shell | 776.5 |

*Equal to 49.91 mg of pure CBD content

**The total weight of the composition of the present invention within a single unit dose is 407 mg. Including the cannabinoid, emulsifier (Tween 80, Dextrin compound and the acid component (pH decreasing agent).

Manufacturing Process

1. The final composition (63250 grams) from manufacturing example 2 is mixed with 750 grams of lactose monohydrate and 650 grams of magnesium stearate.

2. The resulting mixture is sieved through a 500 um sieve and filled into hard gelatin capsules at about 646.5 mg per each capsule.

Example 9

| CBD Beverage example Ingredients | Manufacturing Amounts Kg | Amount in 1 bottle |
|---|---|---|
| CBD | 1 | 94.86 mg* |
| Tween 80 | 6 | 569.26 mg |
| Maltodextrin | 0.7 | 66.4 mg |
| Stearic Acid | 0.45 | 42.69 mg |
| Mint flavor | 0.1 | 9.48 mg |
| apple juice concentrate | 100 | 9.48 ml |
| Water | 2.000 | 189.73 ml |
| Total weight of liquid | 2.108 | 200 ml |

*Equal to about 94.69 mg of CBD per 200 ml of liquid.

Manufacturing Process 1. 8150 grams from the final composition (pre-mix) of manufacturing example 3 is mixed with 100 grams of mint flavor and 2.000 liters of water at about 55° C. for 40 minutes at 200 rpm.

2. The dissolved part of step 1 is separated by filtration so the solubilized part of the mixture can be used in step 3.

3. The water-soluble liquid obtained in step 2 is mixed with 100000 g. of liquid apple juice concentrate.

4. The mixture in step 3 is filled into 220 ml amber glass bottles at 200 ml per bottle.

Example 10

| CBD Chocolate Bar (Food Example) Ingredients | grams | Dose per 20 gram Chocolate Bar in mg |
|---|---|---|
| CBD | 500 | 177.54* |
| Polysorbate 80 | 3000 | 1065.24 |
| Maltodextrin | 350 | 124.27 |
| Aeroperl 300 | 2250 | 798.93 |
| Stearic acid | 225 | 79.89 |
| Chocolate base | 50000 | 17754.1 |
| Total Weight | 56325 | 20.000 |

*Equal to 175.46 mg pure CBD per chocolate bar serving size being 5 grams

Manufacturing Process 1. 50 kilograms of chocolate is melted at about 32 to 47° C. in a jacketed mixing tank.

2. 6325 grams of the final mixture of the composition from manufacturing example no:2 is added to the chocolate in the mixer and mixed for at least 20 minutes 3. The mixture in step 2 is mixed while gradually bringing down the temperature to about 32 to 36° C.

4. The mixture is poured into molds when the mixture is at 29-33° C. until all cavities are filled.

5. The mold is vibrated for about 80 seconds to increase the homogeneous dispersion of the mixture into the cavities.

6. The mold is cooled down for 5 to 8 minutes.

7. The mold is placed in a refrigerator at 8 to 13° C. for about 50 minutes.

8. The mold is turned upside-down to eject the chocolates in the cavities.

9. Finished chocolate bars at about 20 grams per pack, are placed in a sealed aluminum foil packaging.

The invention claimed is:

1. An oral composition comprising at least one cannabinoid compound, at least one emulsifier, and at least one acid compound, wherein the weight ratio of cannabinoid compound to the acid compound is between 5:1 to 1:1 and the weight ratio of emulsifier to the acid compound is between 40:1 to 20:1.

2. The oral composition of claim 1, wherein the acid compound is an organic acid.

3. The oral composition of claim 2, wherein the acid compound is selected from the group consisting of stearic acid, citric acid, gluconic acid (E 574), inosinic acid (E 630), glutamic acid (E620), guanilic acid (E 626), sodium caprate (decanoic acid), dichroic acid (E330), malic acid (E296), acetic acid (E260), tartaric acid (E334), lactic acid (E270), alginic acid (E400), and a mixture thereof.

4. The oral composition of claim 3, wherein the acid compound is stearic acid, decanoic acid, or citric acid.

5. The oral composition of claim 1, wherein the weight ratio of emulsifier to the acid component compound is between 30:1 to 15:1.

6. The oral composition of claim 1, wherein the cannabinoid compound is selected from the group consisting of A9-tetrahydrocannabinol (THC), A8-tetrahydrocannabinol, A9-tetrahydrocannabinol propyl analogue (THCV), cannabidiol (CBD), cannabidiol propyl analogue (CBDV), cannabinol (CBN), cannabichromene, cannabichromene propyl analogue and cannabigerol or derivatives and combinations thereof.

7. The oral composition according to of claim 6, wherein the cannabinoid compound is selected from the group consisting of A9-tetrahydrocannabinol (THC), A9-tetrahydrocannabinol propyl analogue (THCV), cannabidiol (CBD) and combinations thereof.

8. The oral composition of claim 1, wherein the emulsifier is selected from the group consisting of polyoxethylene derivatives, sorbitan esters, polyethylene glycol derivatives and a combination thereof.

9. The oral composition of claim 1, wherein the emulsifier is selected from the group consisting of tearoyl polyoxyl-32 glycerides, lauroyl polyoxyl-32 glycerides or polyoxy-ethylene sucrose diester dimyristate, Polyoxy-ethylene sucrose diester dinnyristate, polyoxy-ethylene sucrose diester dipalmitate, polyoxy-ethylene sucrose diester dioleate, polysorbate 80, polysorbate 60, polysorbate 20, PEG-8 laurate, PEG 400 monoluarate, PEG 10 isooctylphenyl ether, PEG 40 stearate, PEG 50 stearate, PEG 40 isooctylphenyl ether, sodium stearoyl-2-lactylate, sodium stearoyl lactylate and a combination thereof.

10. The oral composition of claim 1, wherein the emulsifier is a polyoxylglyceride or a polysorbate (sorbitan ester).

11. The oral composition according to of claim 10, wherein the emulsifier is selected from the group consisting of stearoyl polyoxyl-32 glycerides, lauroyl polyoxyl-32 glycerides, polysorbate 80, polysorbate 60, polysorbate 20, and a combination thereof.

12. The oral composition of claim 1, further comprising at least one dextrin compound.

13. The oral composition of claim 12, wherein the dextrin compound is selected from the group consisting of maltodextrin, α-cyclodextrin, γ-cyclodextrin, β-cyclodextrin, 2-hydroxypropyl-β-cyclodextrin, sulfobutylether-β cyclodextrin sodium salt, randomly methylated β-cyclodextrin, branched β-cyclodextrin, γ-cyclodextrin and derivatives thereof.

14. The oral composition of claim 13, wherein the dextrin compound is selected from the group consisting of maltodextrin, β-cyclodextrin, 2-hydroxypropyl-β-cyclodextrin, sulfobutylether β-cyclodextrin sodium salt, randomly methylated β-cyclodextrin, and branched β-cyclodextrin.

15. The oral composition of claim 14, wherein the dextrin compound is maltodextrin or β-cyclodextrin.

16. The oral composition of claim 1, further comprising a silica derivative.

17. The oral composition of claim 16, wherein the silica derivative is hydrophilic.

18. The oral composition of claim 16, wherein the silica derivative has a mean particle diameter of between 10 to 250 microns.

19. The oral composition of claim 16, wherein the silica derivative has a BET surface area between 40 to 400 m²/g.

20. The oral composition claim 16, wherein the silica derivative has a tamped density between 50 to 600 g/L.

21. The oral composition of claim 20, wherein the silica derivative has a tamped density between 50 to 400 g/L.

22. The oral composition of claim 16, wherein the silica derivative is selected from colloidal silicon dioxide, calcium silicate, or magnesium aluminometasilicate.

* * * * *